United States Patent

Schönberger et al.

[11] 4,309,551
[45] Jan. 5, 1982

[54] QUATERNIZED, BRIDGED BENZIMIDAZOLYLBENZIMIDAZOLES, PROCESSES FOR THEIR PREPARATION AND THEIR USE

[75] Inventors: Norbert Schönberger, Wehrheim; Erich Schinzel, Hofheim am Taunus; Thomas Martini; Günter Rösch, both of Bad Soden am Taunus, all of Fed. Rep. of Germany

[73] Assignee: Hoechst Aktiengesellschaft, Frankfurt, Fed. Rep. of Germany

[21] Appl. No.: 191,709

[22] Filed: Sep. 29, 1980

[30] Foreign Application Priority Data

Oct. 2, 1979 [DE] Fed. Rep. of Germany ....... 2939916

[51] Int. Cl.³ .................. C07D 235/30; C07D 487/31; C07D 235/04
[52] U.S. Cl. .................................... 548/324; 548/328; 260/245.6
[58] Field of Search .............................. 548/328, 324; 260/245.6

[56] References Cited

U.S. PATENT DOCUMENTS 2,479,152  8/1949  Brooker .......................... 260/245.6

OTHER PUBLICATIONS

Imidazole and its Derivatives, Part I, Klaus Hofmann, Intersci. Publishers, Inc., N.Y., (1953), p. 257.

*Primary Examiner*—John M. Ford
*Assistant Examiner*—Robert C. Whittenbaugh
*Attorney, Agent, or Firm*—Connolly and Hutz

[57] ABSTRACT

Compounds of the general formula (1)

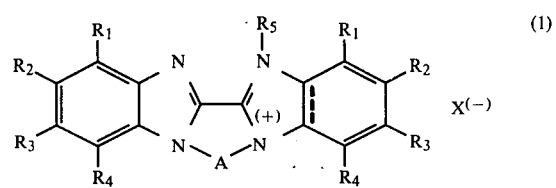

wherein $R_1$ denotes hydrogen, halogen, alkyl, alkoxy or, conjointly with $R_2$, a fused benzo ring, $R_2$ denotes hydrogen, alkyl, alkoxy, halogen, phenyl, cyano, carboalkoxy, carboxyl, carbonamido, monoalkylcarbonamido, dialkylcarbonamido, sulfo, alkylsulfonyl, alkyloxysulfonyl, sulfonamido, monoalkylsulfonamido or dialkylsulfonamido or, conjointly with $R_3$, a fused benzo ring, $R_3$ has the same meaning as $R_2$, $R_4$ denotes hydrogen, alkyl, alkoxy, halogen or, conjointly with $R_3$, a fused benzo ring, $R_5$ denotes alkyl, hydroxyalkyl, alkoxyalkyl, optionally substituted aralkyl, cyanoethyl, cycloalkyl or a group of the formulae —CH$_2$CN, —CH$_2$CONH$_2$ or —CH$_2$COO—alkyl, A denotes a group of the formulae

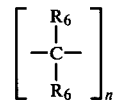

or

—(CH$_2$)$_4$—

$R_6$ denotes hydrogen, alkyl, hydroxyalkyl, alkoxyalkyl, aralkyl or optionally substituted phenyl, n denotes 1, 2 or 3 and $X^{(-)}$ denotes a halide, alkylsulfonate, alkylsulfate, alkylphenylsulfonate or phenylsulfonate ion, and processes for their preparation and their use as optical brighteners.

5 Claims, No Drawings

QUATERNIZED, BRIDGED BENZIMIDAZOLYLBENZIMIDAZOLES, PROCESSES FOR THEIR PREPARATION AND THEIR USE

The invention relates to new, quaternized, bridged benzimidazolylbenzimidazoles of the general formula (1)

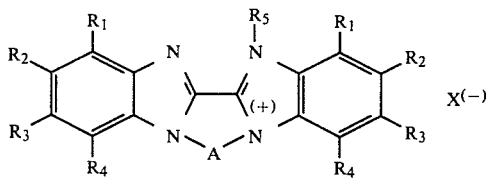

wherein $R_1$ denotes hydrogen, halogen, alkyl, alkoxy or, conjointly with $R_2$, a fused benzo ring, $R_2$ denotes hydrogen, alkyl, alkoxy, halogen, phenyl, cyano, carboalkoxy, carboxyl, carbonamido, monoalkylcarbonamido, dialkylcarbonamido, sulfo, alkylsulfonyl, alkyloxysulfonyl, sulfonamido, monoalkylsulfonamido or dialkylsulfonamido or, conjointly with $R_3$, a fused benzo ring, $R_3$ has the same meaning as $R_2$, $R_4$ denotes hydrogen, alkyl, alkoxy, halogen or, conjointly with $R_3$, a fused benzo ring, $R_5$ denotes alkyl, hydroxyalkyl, alkoxyalkyl, optionally substituted aralkyl, cyanoethyl, cycloalkyl or a group of the formulae —$CH_2CN$, —$CH_2CONH_2$ or —$CH_2COO$-alkyl, A denotes a group of the formulae

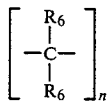

or
—$(CH_2)_4$—

$R_6$ denotes hydrogen, alkyl, hydroxyalkyl, alkoxyalkyl, aralkyl or optionally substituted phenyl, n denotes 1, 2 or 3 and $X^{(-)}$ denotes a halide, alkylsulfonate, alkylsulfate, alkylphenylsulfonate or phenylsulfonate ion.

Preferred compounds of the formula 1 are those wherein $R_1$ denotes hydrogen, alkyl or, conjointly with $R_2$, a fused benzo ring, $R_2$ denotes hydrogen, alkyl, alkoxy, halogen, cyano, carboalkoxy, dialkylcarbonamido, sulfo, alkylsulfonyl, alkyloxysulfonyl, sulfonamido or, conjointly with $R_3$, a fused benzo ring, $R_3$ has the same meaning as $R_2$, $R_4$ denotes hydrogen, alkyl or, conjointly with $R_3$, a fused benzo ring, $R_5$ denotes alkyl, hydroxyalkyl, alkoxyalkyl, optionally substituted aralkyl, cyanoethyl or a group of the formulae —$CH_2CN$, —$CH_2CONH_2$ or —$CH_2COO$-alkyl, A denotes a group of the formulae

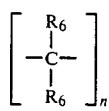

or
—$(CH_2)_4$—

$R_6$ denotes hydrogen, alkyl, hydroxyalkyl, alkoxyalkyl, aralkyl or optionally substituted phenyl, n denotes 1, 2 or 3 and $X^{(-)}$ denotes a halide, alkylsulfonate, alkylsulfate, alkylphenylsulfonate or phenylsulfonate ion.

Particularly preferred compounds are those of the formula (1) wherein $R_1$ and $R_4$ denote hydrogen, methyl, ethyl, methoxy or chlorine or $R_1$ conjointly with $R_2$ and/or $R_3$ conjointly with $R_4$ denote a fused benzo ring, $R_2$ and $R_3$ denote hydrogen, methyl, ethyl, chlorine, alkylsulfonyl, cyano, carboxyl, carboalkoxy or carbonamido, $R_5$ denotes alkyl, hydroxyalkyl, benzyl which is optionally substituted by chlorine, methyl or methoxy, or a group of the formulae —$CH_2CN$, —$CH_2CONH_2$ or —$CH_2COO$-alkyl, A denotes methylene, ethylene, trimethylene or tetramethylene, each of which can be substituted by alkyl, alkoxy, phenyl, cyanophenyl or chlorophenyl, and $X^{(-)}$ denotes a chloride, ethylsulfate, methylsulfate, methylsulfonate, tolylsulfonate or phenylsulfonate ion.

Particularly preferred compounds are also those of the formula (1) wherein $R_1$ and $R_4$ denote hydrogen, $R_2$ denotes hydrogen, alkyl, alkoxy or chlorine, $R_3$ denotes hydrogen, alkyl, alkoxy, chlorine, methylsulfonyl, cyano or carboalkoxy, $R_5$ denotes methyl, A denotes methylene, ethylene or propylene and $X^{(-)}$ denotes chloride, methylsulfate, ethylsulfate, methylsulfonate or p-tolylsulfonate.

Particularly preferred compounds are also those of the formula (1) wherein $R_1$ and $R_4$ denote hydrogen, $R_2$ denotes hydrogen, alkyl, alkoxy or chlorine, $R_3$ denotes hydrogen, if $R_2$ is other than hydrogen, and also denotes alkyl, chlorine, methoxy, ethoxy, methylsulfonyl, cyano or carboalkoxy, $R_5$ denotes methyl, A denotes ethylene and $X^{(-)}$ denotes chloride, methylsulfate, methylsulfonate or tolylsulfonate.

The alkyl and alkoxy groups indicated above and also other groups derived therefrom contain 1 to 4 C atoms in each case. Cycloalkyl preferably denotes cyclohexyl and aralkyl is preferably benzyl. The aralkyl group and also the phenyl group can optionally be substituted by halogen, alkyl or cyano. The substituents in the two benzimidazole rings can in each case be identical or different.

The compounds of the formula (1) are prepared in a known manner by alkylating a compound of the formula (2)

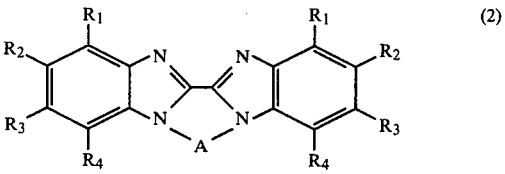

with a compound of the formula

X—$R_5$.

This alkylation is preferably effected in an inert organic solvent, particularly in an aprotic, polar solvent, such as dimethylformamide, at temperatures of approx. 50° to 150° C.

A further process for their preparation consists in cyclizing a compound of the formula (3)

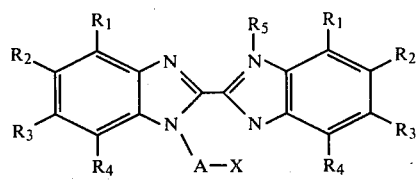

by heating at approx. 50° to 150° C. in an inert organic solvent, if appropriate with the addition of a catalyst. However, the compounds of the formula (1) can also be prepared by cyclizing a compound of the formula (4)

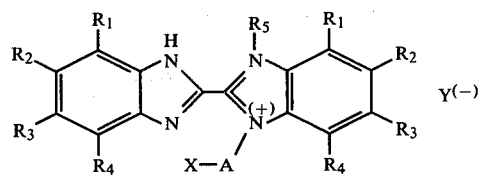

wherein $Y^{(-)}$ denotes a colorless anion, by heating at approx. 50° to 150° C. in an inert organic solvent, if appropriate in the presence of a basic compound. The preparation of the compounds of the formula (1) can also be effected by coupling compounds of the formula (5)

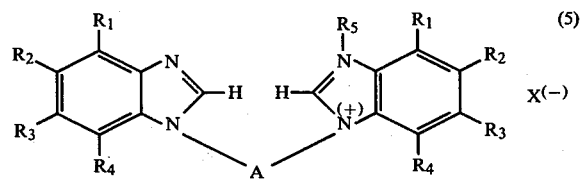

in the 2,2'-position in an oxidative manner.

The benzimidazoles of the formula (2) which are used as starting compounds are obtained by reacting bisbenzimidazoles of the formula (6)

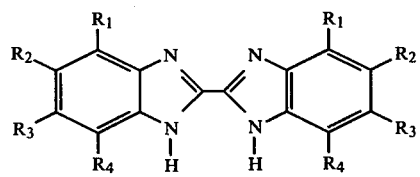

with a compound Z-A-Z wherein Z represents a halogen atom. Examples of this are methylene halides, 1,2-dibromoethane, trimethylene bromide or 1,4-dibromobutane. The addition of a basic compound is advantageous in this reaction. The insertion of the bridge A can, however, also be effected by reacting the compounds of the formula (6) with an alkylene oxide.

Another possible means of preparing the bis-benzimidazoles of the formula (2) consists in reacting a compound of the formula (7)

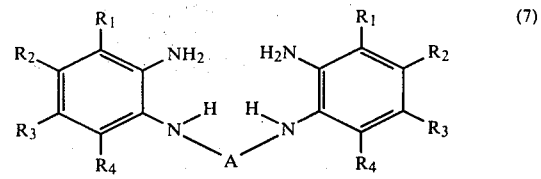

with oxalic acid or an oxalic acid derivative such as, say, oxamide, dicyanogen, an oxalic acid diester or oxalyl chloride.

The bisbenzimidazoles of the formula (2) can also be prepared by linking compounds of the formula (8)

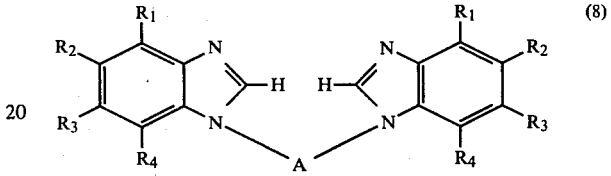

in the 2,2'-position in an oxidative manner in accordance with known processes (B. A. Tertov et al., TETRAHEDRON LETTERS 1968, 4,445).

As a result of the processes used for their preparation, the bridge bisbenzimidazoles of the formula (2), and, accordingly, also the compounds (1) according to the invention, can in theory be obtained both in the symmetrical form and in the unsymmetrical form, that is to say the substituent $R_1$ in one of the benzimidazole rings can be identical with either the substituent $R_1$ or the substituent $R_4$ in the other benzimidazole ring. Correspondingly, one substituent $R_2$ can be identical with the other substituent $R_2$ or with $R_3$. From a purely theoretical point of view, therefore, it is possible for mixtures consisting of the symmetrical and the unsymmetrical compound to be formed. In practice, however, no supporting evidence could be discovered for such an assumption, since all the compounds of the formula (1) prepared have proved to be single substances as shown by chromatography.

The bisbenzimidazoles of the formula (6) can be prepared analogously to the process described by S. Hünig. Ann. 765 (1972), 126, from phenylenediamines and oxalic acid derivatives, such as, say, oxamide, or oxalyl chloride is reacted with o-nitroaminobenzenes, the nitro group is then reduced and the imidazole rings are closed analogously to conventional processes. Another possible means of preparing, above all unsymmetrically substituted, bisbenzimidazoles of the formula (6) consists in reacting a derivative of benzimidazol-2-ylcarboxylic acid, such as, for example, the acid chloride, with suitable phenylenediamines or o-nitroaminobenzenes. The nitro group is then reduced to give the amino group before ring closure.

The new compounds are used for brightening organic material, such as, say, cotton and above all synthetic fibers, for example fibers made from polyesters, such as polyterephthalic acid glycol esters, polyamides, such as polymers based on hexamethylenediamine adipate or caprolactam, cellulose esters, such as cellulose 2½-acetate and cellulose triacetate, and especially polyacrylonitrile.

The organic material can be brightened, for example, by incorporating into it small quantities of optical brighteners according to the invention, appropriately 0.001 to 1%, relative to the material to be brightened, if appropriate together with other substances, such as plasticizers, stabilizers or pigments. The brighteners can, for example, be incorporated into the plastics dissolved in plasticizers, such as dioctyl phthalate, or together with stabilizers, such as dibutyl-tin dilaurate or sodium pentaoctyl tripolyphosphate, or together with pigments, for example titanium dioxide. Depending on the nature of the material to be brightened, the brightener can also be dissolved in the monomers before polymerization, in the polymer composition or, together with the polymers, in a solvent.

The material thus pre-treated is then brought into the desired final form by processes which are in themselves known, such as spinning and stretching. The brighteners can also be incorporated into finishes, for example into finishes for textile fibers, such as polyvinyl alcohol, or into resins or resin precondensates, such as, for example, methylol compounds of ethyleneurea, which are used for textile treatment.

The compounds according to the invention are also suitable for brightening paper by surfacecoating. However, it is preferable to brighten colorless, high-molecular organic material in the form of fibers. For brightening these fiber materials it is advantageous to use an aqueous solution or dispersion of benzimidazoles, according to the invention, of the formula (1). In this case, the dispersion or solution of brightener preferably has a content of 0.005 to 0.5% of benzimidazole according to the invention, relative to the fiber material. In addition, the dispersion or solution can contain auxiliaries, such as dispersing agents, for example condensation products of fatty alcohols or alkylphenols having 10 to 18 carbon atoms, which contain 15 to 25 moles of ethylene oxide, or condensation products of alkylmonoamines or polyamines having 16 to 18 carbon atoms, which contain at least 10 moles of ethylene oxide, organic acids, such as formic acid, oxalic acid or acetic acid, detergents, swelling agents, such as dichlorobenzenes or trichlorobenzenes, wetting agents, such as sulfosuccinic acid alkyl esters, bleaching agents, such as sodium chlorite, peroxides or hydrosulfites, and also, if appropriate, brightening agents of the same or other classes, such as, for example, stilbene derivatives having an affinity for cellulose.

The brightening of the fiber material with the aqueous liquor of brightener is effected either by the exhaustion process at temperatures of, preferably, 30° to 150° C., or by the padding process. In the latter case, the goods are impregnated with, for example, a 0.2 to 0.5% strength dispersion of brightener and the material being dyed is finished, for example, by a dry or moist heat treatment, for example by streaming at 2 atmospheres or, after drying has been carried out, by dry heating at 180° to 220° C. for a brief period, the fabric being thermofixed at the same time, if appropriate. The fiber material treated in this way is finally rinsed and dried.

Colorless, high-molecular organic material which has been optically brightened in accordance with the invention, especially natural or synthetic fiber material which has been brightened by the exhaustion process, has an attractive, pure white appearance with a blue-violet to bluish-tinged fluorescence; material of this kind which has been dyed in light colors and whitened in accordance with the invention is distinguished by a pure color shade.

Wash liquors containing benzimidazoles of the formula (1) impart, during washing, a brilliant appearance in daylight to the textile fibers treated in this way, for example synthetic polyamide, polyester and cellulose fibers, but particularly polyacrylonitrile fibers.

EXAMPLE 1:

In order to prepare the quaternary compound of the formula

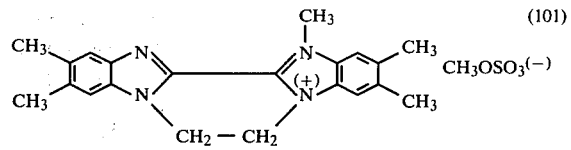

31.6 g of 1,1'-dimethylene-2,2'-bis-(5,5',6,6'-tetramethyl)-benzimidazole are suspended in 300 ml of dimethylformamide. After adding 10 ml of dimethyl sulfate, the mixture is heated for 1 hour at 80° C. and then for 10 minutes at 120° C., while stirring, in the course of which a clear solution is formed. Stirring is continued for 1 hour at 80° C., the mixture is cooled to 5° C. and the reaction product which has precipitated is isolated by filtration. The filter cake containing solvent is washed with toluene and is then dried in vacuo at 60° C. Crude yield: 42.0 g, corresponding to 95% of theory. After recrystallization from methanol, the slightly yellowish compound melts at 346°–350° C., with decomposition.

The compound dissolves both in water and in dimethylformamide to give a blue-violet fluorescence in daylight and is excellently suitable for brightening organic materials, in particular polyacrylonitrile fibers.

The 1,1'-dimethylene-2,2'-bis-(5,5',6,6'-tetramethyl)-benzimidazole used as the starting material is prepared as follows: 11.6 g of 2,2'-bis-(5,5',6,6'-tetramethyl)-benzimidazole are suspended in 200 ml of dimethylformamide together with 13.8 g of potassium carbonate. After adding 4.3 ml of 1,2-dibromoethane the mixture is stirred for 8 hours at 80° C. and then for 6 hours at 100° C. The mixture is allowed to cool to room temperature and is filtered and the filter cake is first washed twice with DMF and is then washed with water. Crude yield after drying at 60° C. in vacuo: 10.1 g. The compound can be recrystallized from glacial acetic acid and then exhibits correct values in elementary analysis. Melting point: 360° C.

The 2,2'-bis-(5,5',6,6'-tetramethyl)-benzimidazole used as the starting material is prepared as follows: 40.8 g of 4,5-dimethyl-1,2-diaminobenzene are suspended in 100 ml of glycol together with 13.2 g of oxamide. The mixture is heated to 180° C. and is stirred at this temperature for 40 hours in a gentle stream of nitrogen, in the course of which a little water distils off. The mixture is then allowed to cool, diluted with 100 ml of ethanol and filtered and the filter cake is washed with ethanol. Drying in vacuo gives 31.2 g of 2,2'-bis-(5,5',6,6'-tetramethyl)benzimidazole, which can be purified further by recrystallization from dimethylformamide. Melting point 360° C.

EXAMPLE 2

In order to prepare the quaternary compound of the formula

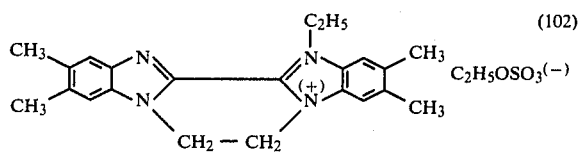

31.6 g of 1,1'-dimethylene-2,2'-bis-(5,5',6,6'-tetramethyl)-benzimidazole are suspended in 300 ml of dimethylformamide. After adding 12 ml of diethyl sulfate the mixture is heated for 2 hours at 80° C., while stirring, in the course of which a clear solution is formed. The mixture is cooled to room temperature and the product which has crystallized out is isolated by filtration. The filter cake is washed twice with a little methanol and is then dried in vacuo at 60° C. Crude yield: 40.0 g, corresponding to 85% of theory. The compound dissolves both in water and in dimethylformamide to give a blue-violet fluorescence in daylight.

EXAMPLE 3

The quaternary compound of the formula

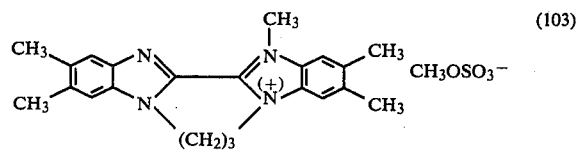

is prepared as follows: 3.3 g of 1,1'-trimethylene-2,2'-bis-(5,5',6,6'-tetramethyl)-benzimidazole are suspended in 35 ml of dimethylformamide. After warming to 100° C., 1 ml of dimethyl sulfate is added and the mixture is stirred for 2 hours at 95°–100° C. A clear, yellowish solution is formed, from which the quaternary reaction product crystallizes out on cooling to room temperature. The product is filtered off and the filter cake is washed with toluene and dried at 60° C. in vacuo. Crude yield: 3.6 g, corresponding to 79% of theory. In a very dilute solution in water or dimethylformamide, the compound, which has a slight yellow color, exhibits a reddish-tinged blue fluorescence in daylight.

The 1,1'-trimethylene-2,2'-bis-(5,5',6,6'-tetramethyl)-benzimidazole used as the starting material is obtained as follows: 14.5 g of 2,2'-bis-(5,5',6,6'-tetramethyl)-benzimidazole are suspended in 250 ml of dimethylformamide together with 16.6 g of potassium carbonate. After adding 12.6 g of 1,3-dibromopropane, the mixture is stirred for 8 hours at 80° to 85° C. and then for a further 19 hours at 100° C. It is cooled to room temperature and filtered and the material on the filter is washed with dimethylformamide and then with water until it is neutral and is dried at 60° C. in vacuo. Crude yield: 5.1 g, corresponding to 31% of theory. The compound is crystallized from dimethylformamide and then exhibits correct values in elementary analysis. Melting point: 360° C.

The preparation of the 2,2'-bis-(5,5',6,6'-tetramethyl)-benzimidazole used as the starting material is described in Example 1.

EXAMPLE 4

The quaternary compound of the formula

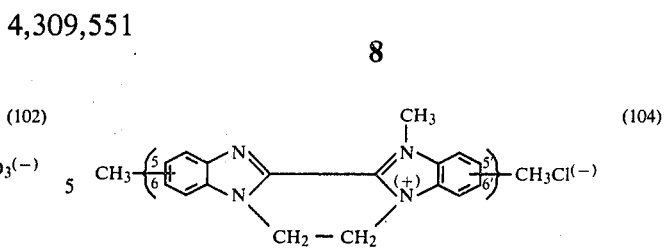

is obtained in the following manner: 20 g of 1,1'-dimethylene-2,2'-bis-(5 or 6, 5' or 6'-dimethyl)-benzimidazole are suspended in 200 ml of dimethylformamide and 7 ml of dimethyl sulfate are added at 100° C. A clear solution is formed, which is stirred for a further 12 hours at 95°–100° C. After cooling, the mixture is diluted with 500 ml of water and is filtered and the filtrate is clarified after being stirred with charcoal. The quaternary compound is precipitated by saturating the solution with sodium chloride and is filtered off and washed with saturated sodium chloride solution. Drying gives 18 g of a yellowish compound which dissolves in hot water to form a clear solution and contains 69% of the quaternary product (104) in addition to sodium chloride and water.

The 1,1'-dimethylene-2,2'-bis-(5 or 6, 5' or 6'-dimethyl)-benzimidazole used as the starting material is prepared as follows: 13.1 g of 2,2'-bis-(5 or 6, 5' or 6'-dimethyl)-benzimidazole are suspended in 150 ml of dimethylformamide together with 17.3 g of potassium carbonate. After adding 5.4 ml of 1,2-dibromoethane the mixture is stirred for 5 hours at 100° C. It is allowed to cool to room temperature and is filtered and the filter cake is washed twice with dimethylformamide and then with water until it is neutral. Crude yield after drying at 60° C. in vacuo: 10.6 g. The compound can be recrystallized from ethylglycol and then exhibits correct values in elementary analysis. Melting point: 360° C.

The 2,2'-bis-(5 or 6, 5' or 6'-dimethyl)-benzimidazole used as the starting material is prepared as follows: 122.2 g of 3,4-diaminotoluene and 44 g of oxamide are suspended in 300 ml of glycol. The mixture is heated to an internal temperature of 195°–200° C. and is stirred for a further 45 hours at this temperature in a gentle stream of nitrogen. The mixture is allowed to cool to room temperature and is diluted with 300 ml of methanol and filtered and the filter cake is washed with methanol. Drying in vacuo gives 70.5 g of 2,2'-bis-(5 or 6, 5' or 6'-dimethyl)-benzimidazole, which can be purified by crystallization from dimethylformamide. Melting point: 360° C.

As a result of this reaction route, the positions 5 and 6 and 5' and 6', respectively, must be regarded as equivalent and it is not possible to state whether the methyl group is located in the 5-position or 5'-position or in the 6-position or 6'-position, respectively. The above method of representation with the curved bracket has therefore been chosen for the final compound.

EXAMPLE 5

In order to synthesize the quaternary compound

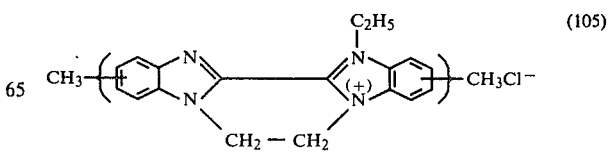

the following procedure is followed: 2.88 g of 1,1'-dimethylene-2,2'-bis-(5 or 6, 5' or 6'-dimethyl)-benzimidazole are suspended in 50 ml of dimethylformamide and 1.4 ml of diethyl sulfate are added at 80° C. The reaction mixture is stirred for a further 5 hours at 80° C. and is allowed to cool to room temperature and then added to a four-fold quantity of water. A small quantity of insoluble impurities is filtered off and approx. 20 g of sodium chloride are added to the filtrate. The product which has crystallized out is filtered off, washed with saturated sodium chloride solution and dried at 60° C. in vacuo. This gives 2.3 g of a nearly colorless compound which dissolves in hot water to give a clear solution and which contains 60% of the quaternary product (105) in addition to sodium chloride and water.

The preparation of the 1,1'-dimethylene-2,2'-bis-(5 or 6, 5' or 6'-dimethyl)-benzimidazole used as the starting material is described in the previous example.

EXAMPLE 6

In order to prepare the quaternary compound of the formula

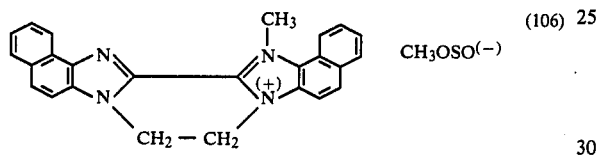

7.2 g of 3,3'-dimethylene-2,2'-bisnaphthimidazole are suspended in 300 ml of dimethylformamide. After adding 2 ml of dimethyl sulfate the mixture is stirred for 2 hours at 80° C., in the course of which a clear solution is formed. The mixture is then cooled to 0° C. and filtered and the filter cake is washed with toluene. Drying in vacuo gives 5.6 g of the desired compound, which can be recrystallized from dimethylformamide. The compound begins to sinter at 348° C. and decomposes above 383° C. When dissolved in dimethylformamide the compound exhibits a powerful blue fluorescence.

The 1,1'-dimethylene-2,2'-bisnaphthimidazole used as the starting material is prepared as follows: 6.7 g of 2,2'-bisnaphthimidazole in 100 ml of dimethylformamide are stirred with 7.0 g of potassium borate and 2.2 ml of 1,2-dibromoethane for 1 hour at 80° C. The mixture is then cooled to 0° C. and the reaction product is filtered off. The filter cake is washed with dimethylformamide, methanol and water until it is free from salts and is then recrystallized from dimethylformamide. Yield: 3.4 g. The crude product exhibits correct values in elementary analysis and melts above 360° C.

The 2,2'-bisnaphthimidazole used as the starting material is prepared as follows: 58 g of 1,2-diaminonaphthalene dihydrochloride, 31.8 g of sodium carbonate and 13.2 g of oxamide are suspended in 100 ml of glycol. The mixture is heated under reflux for 50 hours while stirring and is then allowed to cool, diluted with 100 ml of ethanol and filtered. The filter cake is washed with water, until it is free from salts, and can be purified further by extraction by boiling with glacial acetic acid. Melting point above 360° C.

EXAMPLE 7

In order to prepare the quaternary compound of the formula

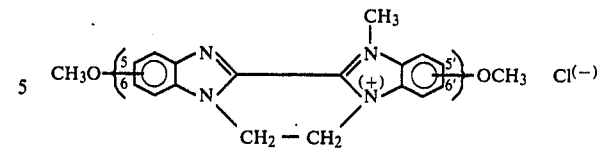

3.2 g of 1,1'-dimethylene-2,2'-bis-(5 or 6, 5' or 6'-dimethoxy)-benzimidazole are suspended in 32 ml of dimethylformamide and the suspension is warmed to 90° C. 1 ml of dimethyl sulfate is added at this temperature and the mixture is kept at this temperature for 3 hours, while stirring. The mixture is cooled to room temperature, 60 ml of water are added, the mixture is filtered and 10 g of sodium chloride are added to the filtrate. The product which has precipitated is filtered off after stirring for a short further period and is rinsed with saturated sodium chloride solution and dried. Crude yield: 5.45 g, containing 34% of sodium chloride, corresponding to 97% of theory.

The compound dissolves in water and dimethylformamide to give a blue fluorescence.

EXAMPLE 8

In order to obtain the following compound

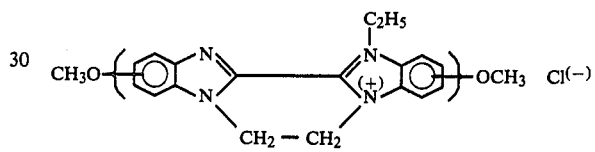

3.2 g of 1,1'-dimethylene-2,2'-bis-(5 or 6, 5' or 6'-dimethoxy)-benzimidazole are suspended in 25 ml of dimethylformamide, 1.3 ml of diethyl sulfate are added and the mixture is stirred for 6 hours at 100° C. 50 ml of water are then added, an insoluble residue is filtered off and the filtrate is allowed to cool. Salting out is effected by means of 8 g of sodium chloride and the precipitate which is formed is filtered off and rinsed with saturated sodium chloride solution. Drying gives 4.5 g of a slightly yellow powder containing 32.3% of sodium chloride. Crude yield: 79.2% of theory.

The compound dissolves in water and dimethylformamide to give a greenish-tinged blue fluorescence.

The 1,1'-dimethylene-2,2'-bis-(5 or 6, 5' or 6'-dimethoxy)-benzimidazole required as the starting material is obtained as follows: 14.7 g of 2,2'-bis-(5 or 6, 5' or 6'-dimethoxy)-benzimidazole are suspended in 100 ml of dimethylformamide together with 16.6 g of potassium carbonate. After adding 5.5 ml of 1,2-dibromoethane, the mixture is stirred at 100° C. for 12 hours under nitrogen. After cooling to room temperature, the precipitate which has been deposited is filtered off and the material on the filter is washed with water until it is neutral. Crude yield: 9.25 g, corresponding to 57.7% of theory. After purification via the hydrochloride, the product has a melting point of 319° to 322° C.

In order to prepare the 2,2'-bis-(5 or 6, 5' or 6'-dimethoxy)-benzimidazole, 106 g of sodium carbonate are added to 211 g of the dihydrochloride of 3,4-diaminoanisole in 600 ml of glycol and, after adding 44 g of oxamide, the mixture is heated at the boil for 72 hours. The dark reaction mixture is cooled to room temperature and the precipitate is filtered off and washed with 300 ml of methanol and a large amount of hot water. Crude yield: 80 g, corresponding to 54.4% of theory. After repeated crystallization from glacial acetic acid and trichlorobenzene, the product has a melting point of 322° to 324° C.

EXAMPLE 9

The following compound

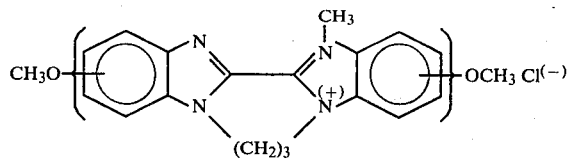

is prepared by stirring 2.5 g of 1,1'-trimethylene-2,2'-bis-(5 or 6, 5' or 6'-dimethoxy)-benzimidazole in 30 ml of dimethylformamide with 0.75 ml of dimethyl sulfate for 8 hours at 100° C. After cooling, the reaction mixture is diluted with 50 ml of water and is filtered and the product is salted out by means of 7 g of sodium chloride. The product which has been precipitated is isolated and washed with saturated sodium chloride solution. Crude yield: 2.9 g, containing 30% of sodium chloride, corresponding to 70.5% of theory.

In water and dimethylformamide the compound exhibits a blue fluorescence in daylight.

The 1,1'-trimethylene-2,2'-bis-(5 or 6, 5' or 6'-dimethoxy)-benzimidazole required as the starting material is obtained by the following route: 14.7 g of 2,2'-bis-(5 or 6, 5' or 6'-dimethoxy)-benzimidazole are suspended in 100 ml of dimethylformamide and, after adding 16.6 g of potassium carbonate and 7.6 ml of 1,3-dibromopropane, the mixture is stirred for 6 hours at 100° C. under nitrogen. It is then cooled to room temperature and filtered and 150 ml of 2 N hydrochloric acid are added to the filtrate. The mixture is heated to the boil and the hydrochloride is allowed to crystallize out while cooling. The free bridged bis-benzimidazole compound is obtained by redissolving the product in water and adding sodium carbonate solution until a slightly alkaline reaction is obtained. Yield: 5.1 g, corresponding to 30.5% of theory. Melting point: 282°-285° C.

EXAMPLE 10

In order to prepare the unsymmetrically substituted compound

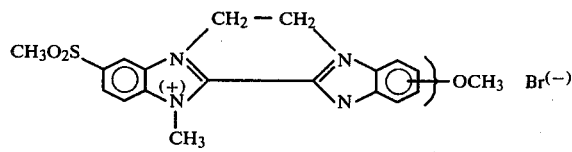

1.07 g of 1-methyl-2,2'-bis-(5-methylsulfonyl, 5' or 6'-methoxy)-benzimidazole in a mixture of 20 ml of dimethylformamide and 10 ml of 1,2-dibromoethane are heated at 100° C. for 10 hours with the addition of 0.6 g of potassium carbonate. The precipitate which has formed is filtered off at room temperature and washed with acetone. After crystallization from water, 0.59 g of a yellow powder with a melting point of 263°-266° C. are obtained, corresponding to a yield of 42.5% of theory.

When dissolved in dimethylformamide, this compound exhibits a powerful blue fluorescence in daylight.

The 1-methyl-2,2'-bis-(5-methylsulfonyl, 5' or 6'-methoxy)-benzimidazole required as the starting material is prepared as follows: 10.17 g of N-methyl-5-methylsulfonylbenzimidazole-2-carboxylic acid are suspended in 50 ml of phosphorus oxychloride, while cooling, 9.16 g of phosphorus pentachloride are added and the mixture is heated to the boil. It is boiled under reflux for 4½ hours, while stirring, and the phosphorus oxychloride is then distilled off in vacuo. The residue is stirred with 300 ml of chlorobenzene and is filtered off and washed with 35 ml of chlorobenzene. The acid chloride thus obtained is suspended in 30 ml of chlorobenzene, 8.4 g of 3-nitro-4-aminoanisole are added and 12.8 g of N,N-dimethylaniline are added dropwise, while stirring. The mixture is then heated to 60° C. and is stirred for 3 hours at this temperature. After cooling, the mixture is filtered and the material on the filter is washed with methanol and water until it is free from chloride ions. Drying gives 11.8 g of the acylamino compound

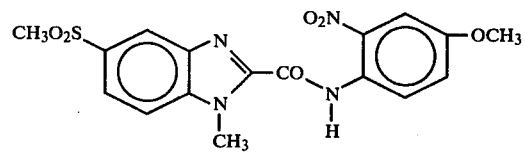

with a melting point of 253°-257° C., corresponding to 73% of theory.

11.23 g of this acylamino compound in 150 ml of dimethylformamide are hydrogenated at room temperature under a pressure of 100 bars in the presence of 1.5 g of Raney nickel. After the catalyst has been filtered off, the solvent is evaporated off and the residue is induced to crystallize by treatment with methanol. Yield: 7.96 g of the compound of the following formula

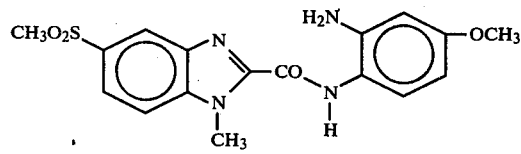

with a melting point of 234°-241° C., corresponding to 77% of theory.

In order to close the benzimidazole ring, 7.96 g of this compound in 40 ml of glacial acetic acid are boiled under reflux for 2½ hours. The reaction mixture is diluted with 40 ml of water and the product is filtered off at room temperature and washed with water. Crude yield: 6.65 g of 1-methyl-2,2'-bis-(5-methylsulfonyl, 5' or 6'-methoxy)-benzimidazole, corresponding to 83.6% of theory. After crystallization from o-dichlorobenzene, the compound of the formula

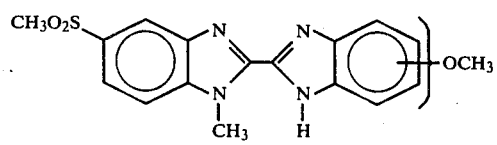

has a melting point of 282°-284° C.

EXAMPLE 11

In order to prepare the unsymmetrically substituted compound

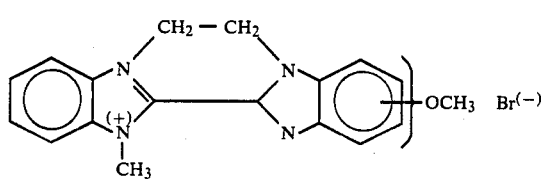

1.39 g of 1-methyl-2,2'-bis-(5' or 6'-methoxy)-benzimidazole are dissolved in 15 ml of dimethylformamide and 0.9 ml of 1,2-dibromoethane and 0.7 g of potassium carbonate are added. The mixture is stirred at 100° C. for 6 hours, cooled to room temperature and diluted with 50 ml of toluene. The reaction product which has precipitated is filtered off and washed with toluene. After crystallization from 70 ml of water, to which charcoal is added, 1.21 g of a yellow powder with a melting point of 278°-285° C., with decomposition, are obtained, corresponding to a yield of 63% of theory.

When dissolved in dimethylformamide, the compound thus obtained exhibits a greenish-tinged blue fluorescent color in daylight.

The 1-methyl-2,2'-bis-(5' or 6'-methoxy)-benzimidazole required as the starting material is obtained by the following route: 14.0 g of N-methylbenzimidazole-2-carboxylic acid are introduced into 100 ml of phosphorus oxychloride at a temperature below 30° C., with slight cooling, 18.3 g of phosphorus pentachloride are added and the mixture is stirred at room temperature for 20 hours. Volatile matter is removed in vacuo at 40°-50° C. and the residue is stirred with 60 ml of toluene, filtered off and washed with toluene. The acid chloride thus obtained is introduced into 70 ml of toluene, 16.8 g of 3-nitro-4-aminoanisole are added and 25.6 g of N,N-dimethylaniline are added dropwise while cooling (30° C.). The mixture is then stirred for 6 hours at 60° C., the solvent is removed in vacuo and the residue is stirred with methanol and filtered off. It is washed with methanol and water and dried at 60° C. in vacuo. 20.3 g of the acylamino compound

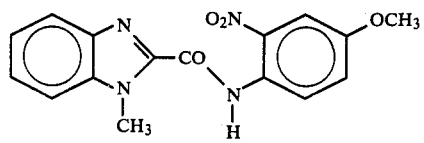

with a melting point of 209°-211° C. are obtained, corresponding to 77% of theory.

The catalytic reduction of this acylamino compound is effected in the manner indicated in Example 10. Yield: 87% of theory, melting point 186°-189° C.

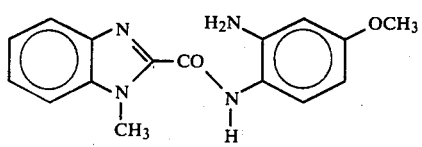

The closure of the benzimidazole ring was also carried out by the procedure indicated in Example 10. 1-Methyl-2,2'-bis-(5' or 6'-methoxy)-benzimidazole was obtained in a crude yield of 96% and, after crystallization from toluene, had a melting point of 245°-247° C.

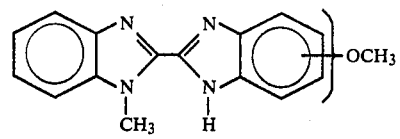

EXAMPLE 12

The compound

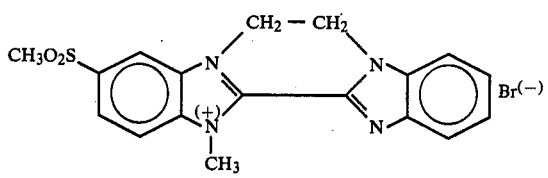

which has a melting point of 326° C., with decomposition, can be prepared analogously to the preceding examples from the following precursors:

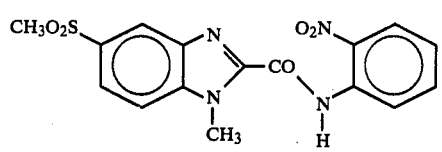

Greenish powder of melting point 250°-251° C., with decomposition.

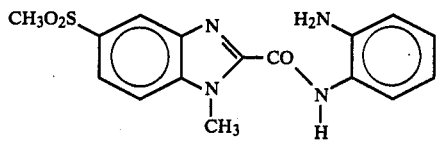

Olive-colored powder of melting point 224°-225° C., with decomposition.

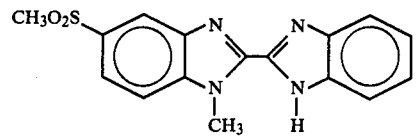

Pale yellow compound with a melting point of 296.5°-298.5° C. (from o-dichlorobenzene).

EXAMPLE 13

0.24 g of sodium chlorite, 0.1 g of a commercially available bleaching auxiliary and 0.3 ml of 2 N acetic acid are dissolved at 60° C. in 200 ml of water. A solution of the optical brightener of the formula (101) is prepared by dissolving 0.02 g in 1 ml of DMF. This solution is poured into the aqueous liquor and the pH value is adjusted to 3.5 by dropwise addition of 10% strength acetic acid. A polyacrylonitrile fabric weighing 5 g is introduced at 60° C. into this aqueous liquor containing the brightener. Preliminary bleaching is first carried out for half an hour at 80° C. and dyeing is then carried out for half an hour at 100° C. The fabric is rinsed with hot and cold water and is dried. The fiber material thus treated exhibits an attractive, white appearance with a violet tint. A similar effect is achived if the process is carried out in the absence of sodium chlorite and the bleaching auxiliary and if the pH value of the liquor is adjusted to 4 with 10% strength acetic acid.

Similar effects are obtained on the fiber material mentioned if a brightener of the formulae (102), (103), (104) or (105) is used instead of the brightener described above, the procedure being in other respects as indicated in the example.

EXAMPLE 14

0.12 ml of 85% strength formic acid are added to 100 ml of water. A solution of the optical brightener of the formula (101) is prepared by dissolving 1 g in 1,000 ml of water. 1.5 ml of this stock solution are added to the solution described above. The liquor thus obtained is warmed to 60° C. and a polyacrylonitrile fabric weighing 3 g is introduced into this liquor. The temperature is increased in the course of 10 to 15 minutes to 95° to 98° C. and the bath is kept at this temperature for one hour. The fabric is then rinsed for 2 minutes in cold, running water and is then dried for 20 minutes at 60° C. The fabric thus treated exhibits a brilliant, white appearance.

Similar results are obtained if the procedure followed is as indicated in the above example, but using the compound of the formulae (102), (103), (104) or (105) instead of the brightener mentioned in the above example.

EXAMPLE 15

If the procedure followed is as in Example 7, but employing, as the brightener, the compound

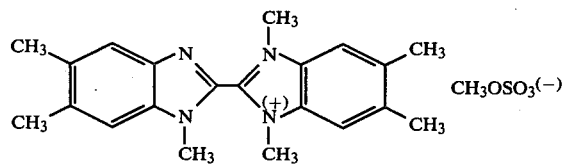

that is to say the compound analogous to (101) without an ethylene bridge, the textile material thus treated exhibits no brightening at all, which shows that only when the ethylene group is introduced does brightening action result.

We claim:
1. A compound of the formula

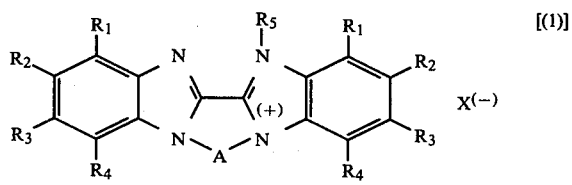

wherein $R_1$ is hydrogen, halogen, alkyl, alkoxy or, conjointly with $R_2$, a fused benzo ring, $R_2$ is hydrogen, alkyl, alkoxy, halogen, phenyl, cyano, carboalkoxy, carboxyl, carbamoyl dialkylcarbamoyl, alkylsulfonyl, alkyloxysulfonyl, sulfonamido, or dialkylsulfonamido or, conjointly with $R_3$, a fused benzo ring, $R_3$ has the same meaning as $R_2$, $R_4$ is hydrogen, alkyl, alkoxy, halogen or, conjointly with $R_3$, a fused benzo ring, $R_5$ is alkyl, hydroxyalkyl, benzyl which may be substituted by chlorine, methyl, or methoxy, cyanoethyl, cycloalkyl or a group of the formulae —$CH_2CN$, —$CH_2CONH_2$ or —$CH_2COO$-alkyl, A denotes a group of the formulae

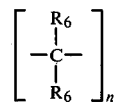

or

—$(CH_2)_4$—

$R_6$ is hydrogen, alkyl, hydroxyalkyl, alkoxyalkyl, benzyl or optionally substituted phenyl wherein the substitutents are selected from the group consisting of halogen, alkyl or cyano, n is 1, 2 or 3 and $X^{(-)}$ is a halide, alkylsulfonate, alkylsulfate, or phenylsulfonate ion and wherein said alkyl and alkoxy groups consist of 1-4 carbon atoms.

2. A compound of the formula

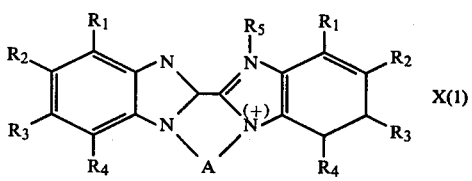

wherein $R_1$ is hydrogen, alkyl or, conjointly with $R_2$, a fused benzo ring, $R_2$ is hydrogen, alkyl, alkoxy, halogen, cyano, carboalkoxy, dialkyl carbamoyl, alkylsulfonyl, alkoxysulfonyl, sulfonamido or, conjointly with $R_3$, a fused benzo ring, $R_3$ has the same meaning as $R_2$, $R_4$ is hydrogen, alkyl or, conjointly with $R_3$, a fused benzo ring, $R_5$ is alkyl, hydroxyalkyl, benzyl which may be substituted by chlorine, methyl, or methoxy, cyanoethyl or a group of the formulae —$CH_2CN$, —$CH_2CONH_2$ or —$CH_2COO$-alkyl, A is a group of the formulae

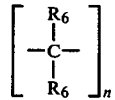

or

—$(CH_2)_4$—

$R_6$ is hydrogen, alkyl, hydroxyalkyl, benzyl or optionally substituted phenyl wherein the substitutents are selected from the group consisting of halogen, alkyl or cyano, n is 1, 2 or 3 and $X^{(-)}$ is a halide, alkylsulfonate, alkylsulfate, or phenylsulfonate ion and wherein said alkyl and alkoxy groups consist of 1-4 carbon atoms.

3. A compound of the formula

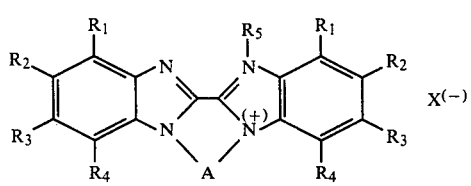

wherein R₁ and R₄ are hydrogen, methyl, ethyl, methoxy or chlorine or R₁ conjointly with R₂ and/or R₃ conjointly with R₄ is a fused benzo ring, R₂ and R₃ are hydrogen, methyl, ethyl, chlorine, alkylsulfonyl, cyano, carboxyl, carboalkoxy or carbamoyl, R₅ denotes alkyl, hydroxyalkyl, benzyl which is optionally substituted by chlorine, methyl or methoxy, or a group of the formulae —CH₂CN, —CH₂CONH₂ or —CH₂COOO-alkyl, A is methylene, ethylene, trimethylene or tetramethylene, each of which can be substituted by alkyl, alkoxy, phenyl, cyanophenyl or chlorophenyl, and X⁽⁻⁾ denotes a chloride, ethylsulfate, methylsulfate, methylsulfonate, tolylsulfonate or phenylsulfonate ion and wherein said alkyl and alkoxy groups consist of 1–4 carbon atoms.

4. A compound of the formula

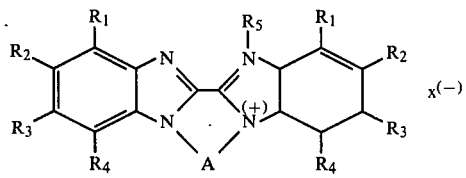

wherein R₁ and R₄ are hydrogen, R₂ is hydrogen, alkyl, alkoxy or chlorine, R₃ is hydrogen, alkyl, alkoxy, chlorine, methylsulfonyl, cyano or carboalkoxy, R₅ is methyl, A is methylene, ethylene or propylene and X is chloride, methylsulfate, ethylsulfate, methylsulfonate or p-toyl-sulfonate and wherein said alkyl and alkoxy groups consist of 1–4 carbon atoms.

5. A compound of the formula

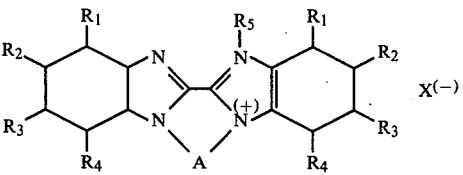

wherein R₁ and R₄ are hydrogen, R₂ is hydrogen, alkyl, alkoxy or chlorine, R₃ is hydrogen, if R₂ is other than hydrogen, and also alkyl, chlorine, methoxy, ethoxy methylsulfonyl, cyano or carboalkoxy, R₅ is methyl, A is ethylene and X⁽⁻⁾is chloride, methylsulfate, methylsulfonate or tolylsulfonate and wherein said alkyl and alkoxy groups consist of 1–4 carbon atoms.

* * * * *